United States Patent
Esher et al.

(10) Patent No.: US 7,791,355 B1
(45) Date of Patent: Sep. 7, 2010

(54) NEAR FIELD FREE SPACE ANISOTROPIC MATERIALS CHARACTERIZATION

(75) Inventors: Justin Esher, Colorado Springs, CO (US); Nicholas Gamroth, Chicago, IL (US); James Dean, Hanscom AFB, MA (US); John S. Derov, Lowell, MA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 321 days.

(21) Appl. No.: 11/998,980

(22) Filed: Oct. 30, 2007

(51) Int. Cl.
*G01R 27/32* (2006.01)
(52) U.S. Cl. .................. 324/637; 324/639; 324/642
(58) Field of Classification Search .............. 324/637, 324/639, 642
See application file for complete search history.

(56) References Cited

U.S. PATENT DOCUMENTS

| | | | |
|---|---|---|---|
| 4,274,048 A * | 6/1981 | Tricoles et al. .............. 324/637 |
| 5,841,288 A * | 11/1998 | Meaney et al. .............. 324/639 |
| 6,097,333 A | 8/2000 | Otto et al. | |
| 6,191,744 B1 * | 2/2001 | Snow et al. ................. 343/703 |
| 6,480,141 B1 * | 11/2002 | Toth et al. ..................... 342/22 |
| 6,674,292 B2 | 1/2004 | Bray et al. | |
| 6,788,244 B1 | 9/2004 | Tam | |
| 6,825,647 B2 | 11/2004 | Kranitzky | |
| 6,842,010 B2 | 1/2005 | Biernacki | |
| 6,850,851 B1 * | 2/2005 | Fourestie et al. .............. 702/65 |
| 6,859,046 B2 * | 2/2005 | Schajer ....................... 324/637 |
| 6,859,047 B2 | 2/2005 | Hemming et al. | |
| 7,057,743 B2 | 6/2006 | Merkel et al. | |
| 7,443,170 B2 * | 10/2008 | Garreau et al. .............. 324/501 |
| 2001/0052779 A1 * | 12/2001 | Okazaki ..................... 324/637 |
| 2005/0128150 A1 * | 6/2005 | Chen .......................... 343/702 |

* cited by examiner

*Primary Examiner*—Timothy J Dole
*Assistant Examiner*—John Zhu
(74) *Attorney, Agent, or Firm*—AFMCLO/JAZ; Gerald B. Hollins; Daniel J. Krieger (57) ABSTRACT

An automated computer controlled electrical materials characterization system in which a material sample is subjected to focused near field polarization controlled microwave electrical energy radiation. Response of the material sample to either of reflected or transmitted/refracted microwave radiation is determined by a microwave energy sensor disposable in a range of physical locations with respect to the sample. Automated and unattended operation of the characterization system by way of disclosed computer software is provided. Computer positioned, lens equipped, microwave antenna horn elements provide source and reception functions for the sample received and discharged microwave radiation. Output signal polarization response from the sample examination is especially considered. The disclosed system is especially suited to characterization of "negative index" electrical materials and has utility with a variety of other materials.

27 Claims, 6 Drawing Sheets

Back  Front  Fig. 6b

NEAR FIELD FREE SPACE ANISOTROPIC MATERIALS CHARACTERIZATION

RIGHTS OF THE GOVERNMENT

The invention described herein may be manufactured and used by or for the Government of the United States for all governmental purposes without the payment of any royalty.

BACKGROUND OF THE INVENTION

Materials with anisotropic electrical properties are of significant interest in the electronic warfare community. Such materials find utility in defending aircraft and related vehicles from electronic discovery as a result of their ability to achieve oppositely signed index of refraction characteristics. These "negative index" materials also have the potential to create cheaper, lighter, and more simplistic phased array radar systems for example. Most materials of these characteristics are in fact man-made and may be based on such fabricated arrangements as dispersion of split ring resonator and thin wire "post elements" into a composite material. The resulting material has negative permeability from the split ring resonators and negative permittivity from the post elements within a specifically designed passband and is thus considered a negative index material. Otherwise the material has positive permeability and permittivity characteristics in lieu of "anisotropic characteristics" attending negative index materials.

Materials of this nature are thusly of current importance in the more fundamental and research oriented work of the electronic community. It has been found however that the laboratory apparatus used to characterize positive index electromagnetic materials are not well suited to characterize the anisotropic nature of positive or negative index materials. A part of this difficulty may be attributed to measurements involving the physical disposition of transducers into physical locations, with respect to a sample, that are simply different from the locations needed for isotropic positive index materials. More subtle however is the fact that the signals emitted from samples of anisotropic positive and the unique properties of negative index materials can be so different from anisotropic positive materials as to be susceptible to being totally missed or ignored during an investigation without the use of enhanced measuring apparatus. This is the area of concern in the present invention.

Horn antennas may be used to focus radiated electrical energy on-to and through a tested material sample in order to discern certain such electrical properties of the sample. The underlying purpose of focusing an electrical energy beam in this way is for example to measure electrical reflection and transmission properties of the material—preferably in a manner that is more easily accomplished as compared to such traditional near field techniques as anechoic chamber measurements. Such traditional near field anechoic chamber measurements often for example dissipate or absorb a reflected wave from a sample under test. With focusing horn antennas, such near field data is readily available, typically allowing for effective permeability and permittivity characteristics to be determined over a broad range of measuring frequencies.

A spot focusing horn lens antenna measurement system may be achieved through manually adjusting the distance between energy transducer horns and the sample material in order to maximize effects of the transmitted and received electrical energy. In previous such system configurations, in order to make off-axis energy measurements, either the horn or the material sample require manual adjustment in order to achieve desirable measuring accuracy.

A primary focus of the present invention is to automate a horn antenna based material characterization process, as well as provide further measurement capabilities in characterizing anisotropy and antenna polarization rotation measurements.

SUMMARY OF THE INVENTION

The present invention provides improved measurement of several radiated energy discerned electrical properties for a variety of electrically useful materials.

It is therefore an object of the invention to improve the accuracy of measuring certain radiated electrical energy responsive properties in naturally occurring and man-made physical materials.

It is another object of the invention to improve the speed of measuring these radiated electrical energy responsive properties in physical materials.

It is another object of the invention to reduce the cost of measuring radiated electrical energy responsive properties in naturally occurring and man-made physical materials.

It is another object of the invention to provide for measurement of both transmitted and reflected radiant electrical energy properties in electrical material samples.

It is another object of the invention to provide a method for measuring radiated electrical energy responsive properties in electrically useful materials.

It is another object of the invention to provide an apparatus for measuring radiated electrical energy responsive properties in electrical materials.

It is another object of the invention to identify readily available components to achieve an automated apparatus and method for measuring radiated electrical energy responsive properties in electrical materials.

It is another object of the invention to provide desirable measurement of permeability, permittivity (i.e., dielectric constant), anisotropy and other electrical properties in samples of electrically useful materials.

It is another object of the invention to provide automated near field evaluation of negative index of refraction electromagnetic materials involving negative permeability and negative permittivity characteristics.

It is another object of the invention to provide a laboratory apparatus that may be easily arranged for routine high volume measurement of selected properties in samples of electrically useful materials.

It is another object of the invention to provide an automatic software controlled electrical material characterization apparatus and method.

It is another object of the invention to provide an anisotropic characteristic responsive materials characterization arrangement.

It is another object of the invention to provide a materials characterization arrangement that is responsive to both positive and negative indexed materials characteristics.

It is another object of the invention to provide a material characterization system operating with the aid of spot focused, horn sourced, microwave spectrum radiant energy.

It is another object of the invention to provide a "start it" then "forget it" until completed automated apparatus for characterizing an electrical material sample.

It is another object of the invention to provide a wide range material polarization responsive automated characterization apparatus.

It is another object of the invention to obtain uninterrupted angular sweep measurements on tested materials with over 330 degrees of independent source/receive horn rotation.

It is another object of the invention to increase electrical materials characterization system capacity by providing for larger and heavier objects to be tested than have been previously possible.

It is another object of the invention to provide for electrical materials characterization of samples greater than 12 inches cubed in size and greater than 150 pounds in weight.

These and other objects of the invention will become apparent as the description of the representative embodiments proceeds.

These and other objects of the invention are achieved by near field focusing horn beamed, spot microwave energy responsive electrical material examination apparatus comprising the combination of:

a plurality of commonly focused microwave transducer horn antenna elements each disposed on a distinct selected trajectory first drive type responsive movable element of said material examination apparatus;

a focused spot microwave electrical energy responsive material sample capturing apparatus disposed in a central near field location with respect to said horn antenna elements selected trajectory in said material examination apparatus;

each said selected trajectory first drive type responsive movable element of said material examination apparatus further including both a second drive type responsive transducer horn antenna element radial distance with respect to said material sample capturing apparatus adjustment and a third drive type responsive microwave transducer horn antenna element signal polarization angle selection apparatus;

a first of said commonly focused microwave transducer horn antenna elements being a source of microwave electrical energy spot focused on said microwave electrical energy responsive material sample and a second of said commonly focused microwave transducer horn antenna elements comprising a microwave receiver apparatus also spot focused on said microwave electrical energy responsive material sample with one of said focused microwave transducer horn antenna elements being first drive type responsive around said trajectory with respect to another of said focused microwave transducer horn antenna elements;

programmed electronic computer apparatus connected with said first second and third drive types and in established sequence control of said material examination apparatus following an operator initiation event;

said selected trajectory first drive type responsive movable elements and related of said antenna horn elements being accommodative of both positive index and negative index electrical characteristic determined signals received from said focused spot microwave electrical energy responsive captured material sample.

BRIEF DESCRIPTION OF THE DRAWINGS

The accompanying drawings incorporated in and forming a part of the specification, illustrate several aspects of the present invention and together with the description serve to explain the principles of the invention. In the drawings:

FIG. 6 includes the views of FIG. 6a and FIG. 6b and shows slab and wedge cross section test samples along with back and front views of the test sample structure respectively.

DETAILED DESCRIPTION OF THE INVENTION

Figure 1:
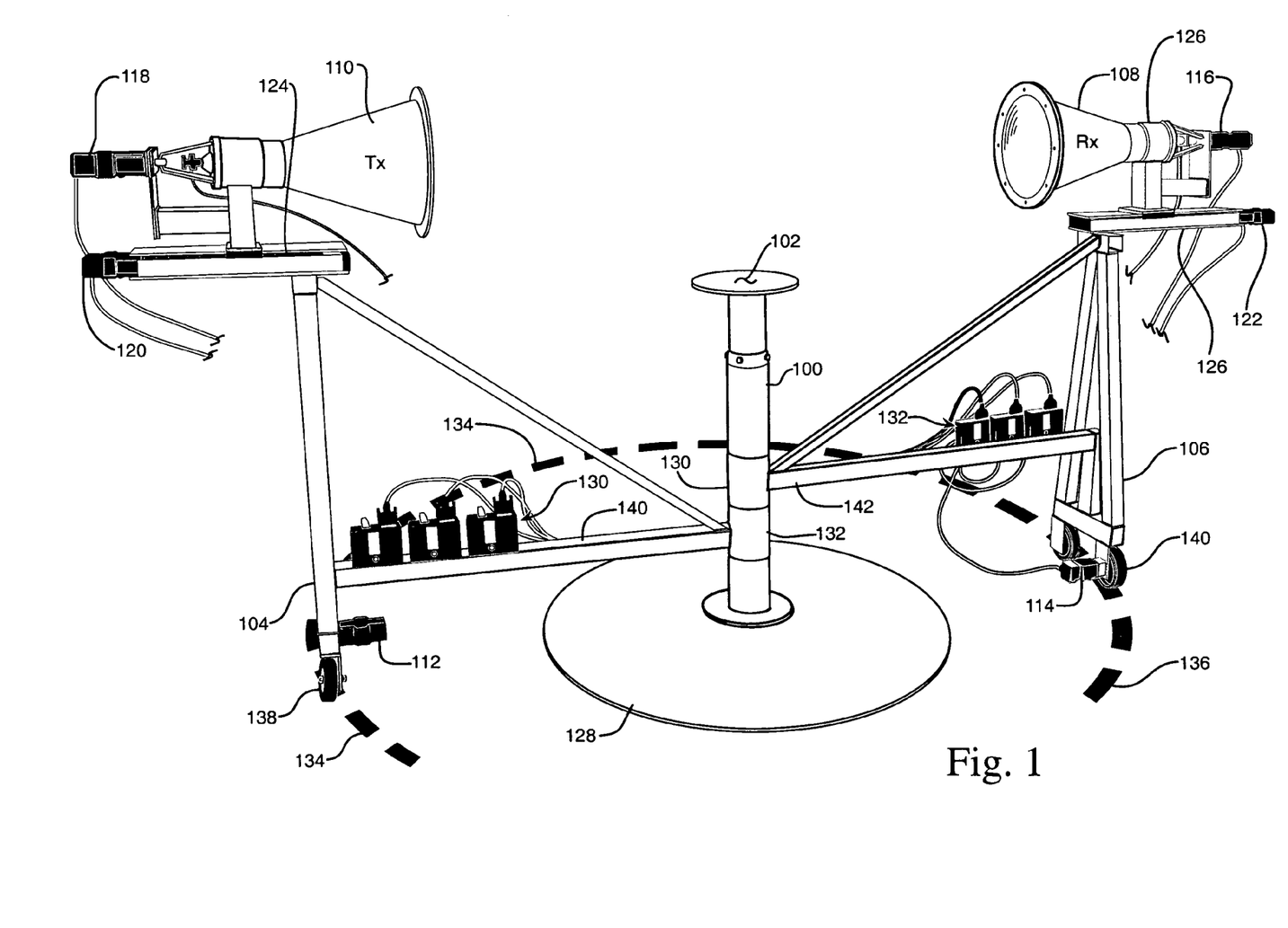
FIG. 1 shows an overall view of a laboratory apparatus according to the present invention.

FIG. 1 in the drawings shows an overall view of a laboratory materials characterization apparatus according to the present invention. In the FIG. 1 drawing there appears a group of mechanical components including a height adjustable pedestal assembly 100, an assembly having an electrical material sample supporting platform 102 and a pair of radially disposed, azimuthally displaceable radio frequency horn supporting uprights 104 and 106. Transmitting and receiving horn antenna elements 110 and 108 respectively are mounted on the uprights 104 and 106. The pedestal assembly 100 is supported on a central floor plate member 128 and includes two pedestal shaft slip joints 130 and 132 enabling accurate but free azimuthal displacement of the two uprights 104 and 106 along circular trajectories indicated at 134 and 136. The trajectories 134 and 136 may be of the same or differing circular radii as discussed later herein. Before continuing with additional description of the FIG. 1 apparatus it is believed helpful to an understanding of the apparatus and its use to consider certain specific details concerning materials that are of special characterization interest with the FIG. 1 apparatus. Such details are believed to be of assistance in appreciating the apparatus to be described and the process it enables. The following several paragraphs are believed appropriate for this purpose.

Figure 5:
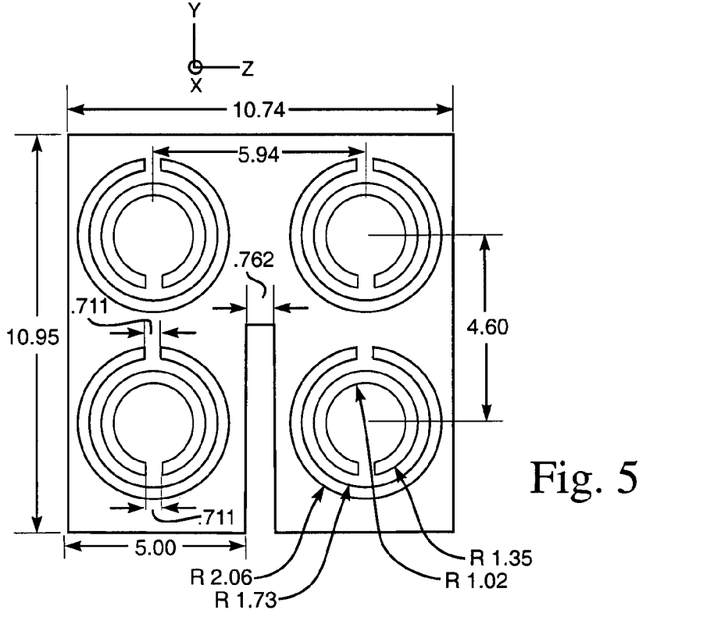
FIG. 5 shows an array of millimeter dimensioned split ring resonators used in negative index anisotropic test materials.

Anisotropic characteristics, involving materials having unequal physical properties along different measurement axes, are of current interest in the electronic warfare community as has been briefly discussed previously herein. One group of such materials, relevant to the microwave frequency spectrum, may be achieved through addition of plural "split ring resonators", resonators as shown in FIG. 5 herein, to an otherwise electrically insulating or dielectric material. These resonators may consist simply of printed circuit-achieved electrical conductors of frequency-selected dimensions, dimensions as appear in metric form in the FIG. 5 drawing for Ku band resonance for example. These FIG. 5 resonators may be provided with negative permeability characteristics by way of the split ring resonator properties. In order to also add negative permittivity properties to these resonators an array of "posts" or thin wire electrical conductors may be added to a segregated rear surface of the resonators. With the addition of these two resonant conductor forms to a dielectric material, an incident electromagnetic energy wave of appropriate microwave frequency is influenced with respect to the magnetic and electrical two characteristics, permeability and permittivity, that are of special current technology interest.

Figures 6, 6A, 6B:
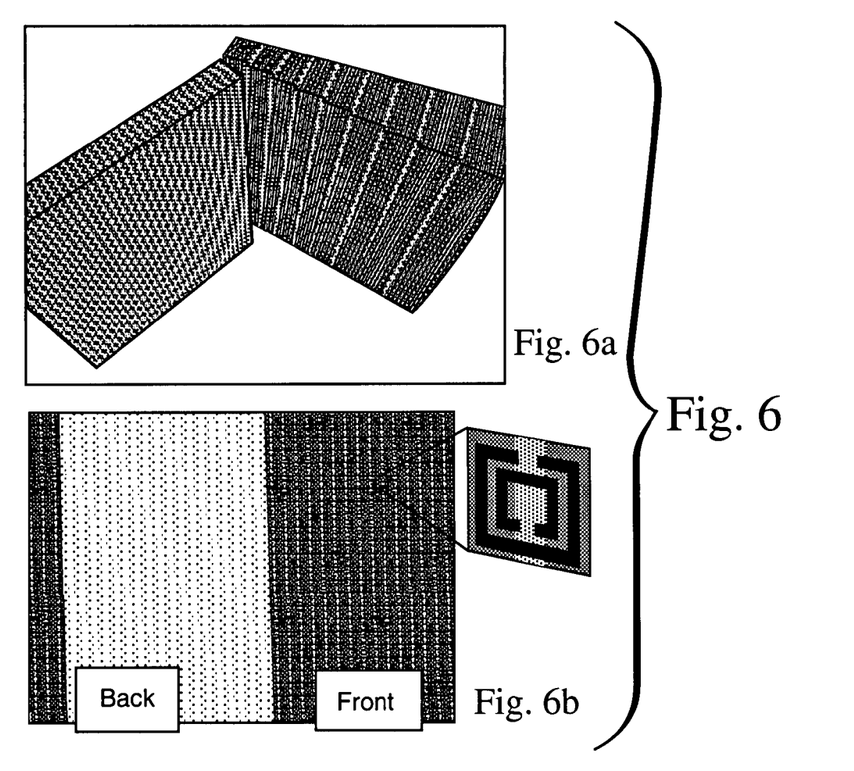

With respect to negative index material or media, a split ring resonator provides a magnetic moment at resonance producing a negative media permeability. The split ring resonator is beneficially combined with for example a wire post array that provides the negative permittivity then contributing to a negative index medium. In the FIG. 6b drawing a printed circuit board is shown with an array of split ring resonators printed on the front of the board and an array of posts printed on the back of the board. An expanded view of one 3.7 millimeter by 3.7 millimeter unit cell forming the array is also shown in FIG. 6b. The FIG. 6b printed circuit board may be cut and assembled into the cavities of for example eight inch by ten inch slab and wedge structures shown in the FIG. 6a drawing of test samples suitable for the FIG. 1 apparatus. Such structures can then be placed in the measurement environment shown in FIG. 1 to be evaluated.

Figure 7:
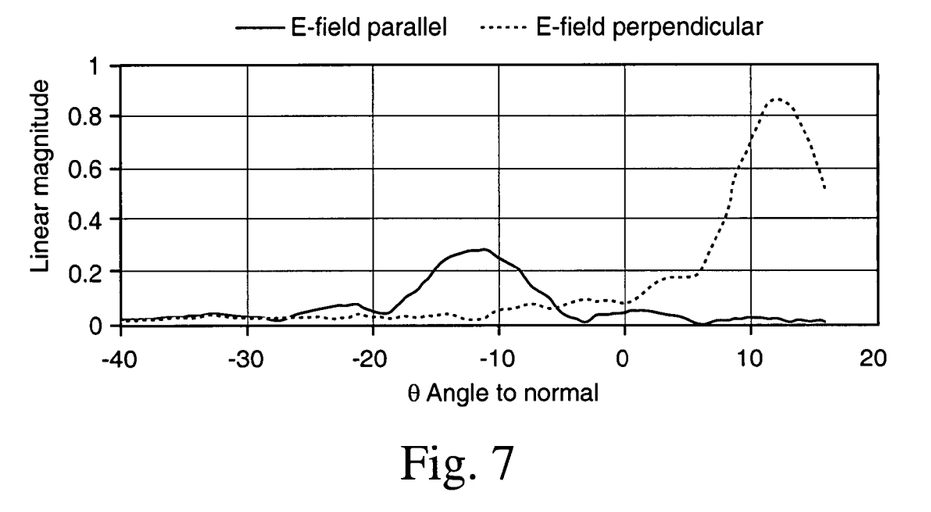
FIG. 7 shows two 13.5 gigahertz anisotropic electrical characteristics of a wedge split ring and post present invention test sample.
Figure 8:
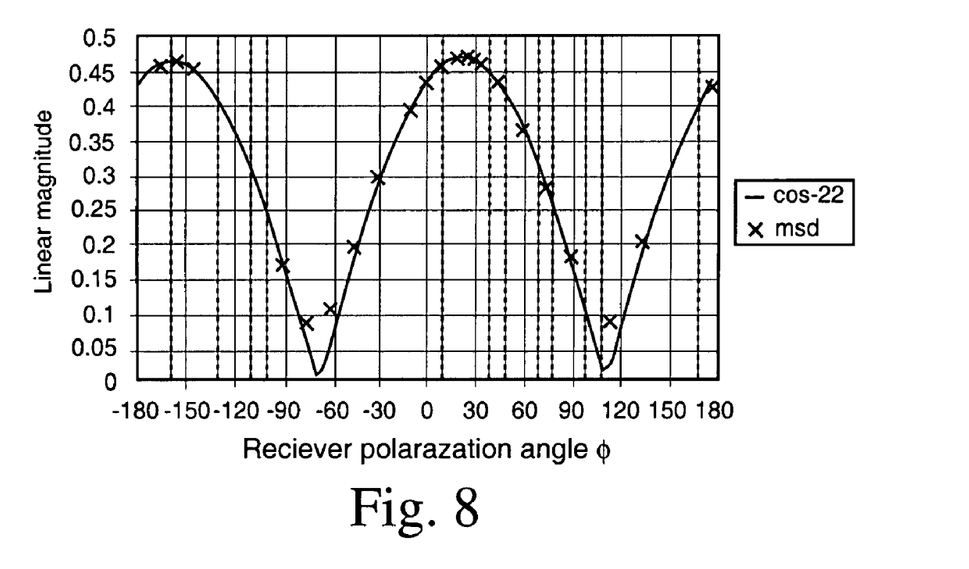
FIG. 8 shows 13.5 gigahertz polarization characteristics for a 12 degree wedge present invention test sample in response to receiving antenna rotation.
Figure 9:
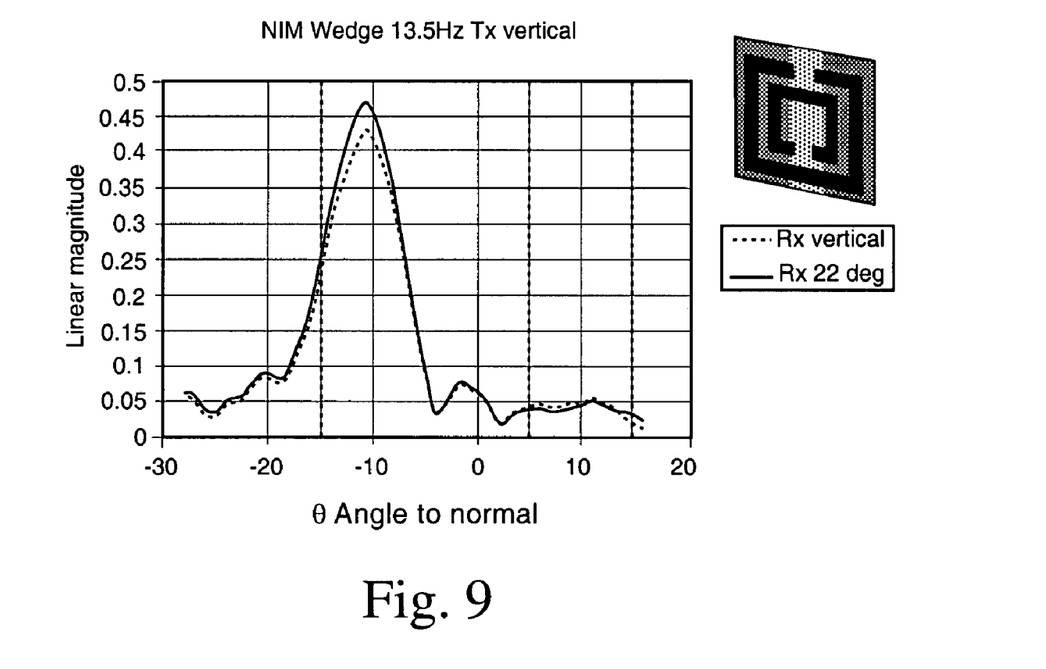
FIG. 9 shows 13.5 gigahertz polarization characteristics for a NIM wedge present invention test sample in response to transmitter antenna rotation.

FIG. 7 through FIG. 9 in the drawings illustrate the results of present invention measurements and the importance of being able to control the polarization angle in the FIG. 1 instrument in order to characterize the anisotropic properties of negative index materials. FIG. 7 for example shows 13.5 gigahertz anisotropy characteristics for a split ring and post wedge sample, of the type shown in the right hand portion of FIG. 6a, and demonstrates that the ability to orient the polarization angle of the transmit horn is desired. In FIG. 7 with polarization of the transmit horn parallel to the wire posts of the split ring and post material negative refraction is observed as is shown by the leftmost and lower curve peak. When the polarization of the transmit horn is rotated so it is perpendicular to wire post of the material then positive refraction is observed as appears in the curve with rightmost peak value of 0.83. FIG. 7 thus shows an extreme anisotropy in the tested material and provides one illustration of need for the material characterization enabled by the FIG. 1 apparatus.

Another illustration may be found in the FIG. 8 drawing where the polarization response of a twelve degree wedge test sample as in FIG. 6a is mapped with respect to the receiver horn 108 in FIG. 1. The map is made by setting the polarization of the 13.5 gigahertz transmit (Tx) horn 110 parallel to the test sample wire posts, so negative refraction is observed, and then varying the polarization of the receiver (Rx) horn. Here the zero degree location is defined by the polarization of the Rx horn being set parallel to the wire posts. The FIG. 8, the Rx horn is rotated one hundred eighty degrees in each direction to map the beam intensity as a function of polarization angle. The resulting plot is then fit with a cosine function to determine the angle of the maximum intensity.

The FIG. 1 apparatus also allows one to map the polarization rotation of the beam through the material. FIG. 9 therefore shows 13.5 gigahertz beam refraction through a NIM wedge with the polarization angle of the Rx horn 108 set to zero degrees and with the polarization angle, $\phi$, of twenty two degrees being the polarization angle location of the maximum intensity of the negatively refracted beam. The FIG. 9 negative refraction peak is shown to occur at an angle, $\theta$ within the FIG. 1 trajectories 134 and 136, of about negative eleven degrees. Since an important property of the tested material is its return loss and insertion loss, it is desirable to have the ability to characterize material polarization behavior and allow the transmitted beam maximum intensity to be determined as is illustrated in FIG. 9. These abilities are an underlying consideration in arranging the FIG. 1 apparatus.

Polarization change in an incident electromagnetic wave as a result of an encounter with the anisotropic material is thus a first material characteristic of interest in the present invention. A second of these characteristics involves refraction based changes in the incident electromagnetic wave as a result of the encounter with an anisotropic material; in other words consideration of the electromagnetic energy emerging after travel through the material. In presently discussed materials this energy is oriented in a direction significantly different than that observed in most naturally occurring materials for example. This latter phenomenon involves electromagnetic energy emergence on an opposite side of a normal drawn to the point of emergence as opposed to most positive electrical characteristics materials and hence leads to the accepted classification of such materials as being of "negative index" character. More precisely, the index of refraction is the square root of the product of permittivity and permeability and the negative index refers to the permittivity and the permeability both being negative. It of course remains true that the material's response to an electric field relates to its permittivity and its response to a magnetic field relates to permeability. Notably such negative index material is characterized by entering and emerging energy each residing on the same side of a normal to the material surface.

In using these materials it is of course desirable to have precise knowledge of their electromagnetic characteristics in order, for example, to select appropriate shapes and sizes for use in an electromagnetic energy beam steering device or for production of radar- invisible aircraft or land vehicle at a predetermined frequency. Upon investigation however it has been found that characterization of materials in these manners has been previously accomplished using apparatus best considered to be of a manually operated nature and also most accommodative of positive index electrical characteristics. Notably, wide ranging polarization, negative electrical characteristics index accommodation and operation in automated characterization equipment cycles have been beyond apparatus of this type. Such is also an area of interest in the present invention.

Returning now to discussion of the FIG. 1 apparatus, also appearing in the FIG. 1 drawing are the radio frequency horn antenna elements 108 and 110 supported on the uprights 104 and 106 for independent-separate or concurrent joint movement along the trajectories 134 and 136. Movement along trajectories 134 and 136 is achieved through rotation of the tire equipped wheels 136 and 138 used in pairs in support of each of uprights 104 and 106. One of these tire equipped wheels in each pair is connected to an azimuth position determining drive motor assembly as indicated at 112 and 114 in the FIG. 1 drawing. The tire for each of the driven wheels is preferably made from a different resilient material from that used in the adjacent non-driven wheel, a material such as serrated rubber tread has been found desirable for this torque-subjected tire frictional engagement tire while a conventional rubber tire suffices for the passive wheel.

It may be appreciated from a visual examination of particularly the FIG. 1 drawing that the possible range of azimuth examination of signals originating in a sample under test is limited to some angular measurement less than a full circle of 360 degrees in arc size. This limitation occurs through the possibility of collision interference between the uprights 104 and 106 and the connected radial arms 140 and 142. It is found in practice that azimuth arcs some 27 degrees short of a 360 degree arc may be reasonably achievable using the structural configurations shown in the FIG. 1 and FIG. 2 drawings and that for most material characterizations this range of azimuth characteristics is satisfactory. It appears additionally possible however that with the use of a degree of mechanical ingenuity it is possible to achieve azimuth arcs meeting or exceeding the 360 degree theoretical azimuth limit can be achieved in such a structure. Avoidance of the illustrated floor-engaging tire structure and use of non colliding vertically segregated supporting elements for uprights 104 and 106, uprights of different radial separation from a central pedestal support 100, appear to offer two avenues by which a greater azimuth arc range of material signal inputs may be accomplished.

The FIG. 1 drive motor assemblies 112 and 114 may include a stepping motor and feedback elements in order to precisely move one or more of the horn elements 108 and 110 along the FIG. 1 illustrated concurrent trajectories 134 and 136 in an accurately controllable manner. Additional drive motor assemblies 120 and 122 in FIG. 1 control the position of radio frequency horns 108 and 110 along radially adjustable radio frequency horn positioning lead screw elements contained at 124 and 126 and shown in FIG. 2 in order to precisely focus each horn on a tested material sample of selected size captured on the sample supporting platform 102. Fundamentally similar drive motor assemblies 116 and 118 may be used to control the horn axis rotated position of each radio frequency horn 108 and 110 in order to control the polarization pattern of the radio frequency energy spot focused on the captured electrical material sample under test and hence provide access to polarization determined material characteristics. These computer controlled polarization related capabilities of the present invention are believed to be significant improvements to the measurement art achieved in the present invention. Sources of electrical energization for each of the stepping motor drive assemblies are indicated at 130 and 132 in the FIG. 1 drawing and are more fully described subsequently herein. An array of electrical conductor cables conveys both energizing and data related signals among the thus-far described elements of the FIG. 1 apparatus.

The drive motor assemblies shown in FIG. 1 enable this apparatus to automatically locate radio frequency emissions originating in a microwave radio frequency signal passing through or reflecting from a material sample held captive on the platform 102. Such signals are of course either refracted by or reflected from an initial course of signal incidence on the tested sample into an angularly deflected signal that is dependent on the tested material characteristics. The precise azimuthal or spatial location of these refracted or reflected radio frequency signals with respect to the tested sample, the polarization of these signals and the relative magnitude of these signals represent the sought-after and sample identity defining characteristics data of testing accomplished according to the invention. Such data may include multi dimensional disposed data components and notably may relate to both positive and negative index characteristics in the tested electrically useful materials. From the apparent physical size of the FIG. 1 elements it may be appreciated that the apparatus is preferably arranged to consider near field electrical characteristics of a tested material sample; preferred dimensions for the FIG. 1 apparatus in fact locate the microwave antenna horns 108 and 110 such that their energy emitting or receiving large diameter ends are disposed substantially three feet from the involved tested material surfaces.

Generally the metallic parts shown in the FIG. 1 drawings may be fabricated as welded aluminum structures. The slip joint elements 130 and 132 may include machined low friction organic materials such as the Teflon or other materials in selected friction abatement locations.

Figure 2:
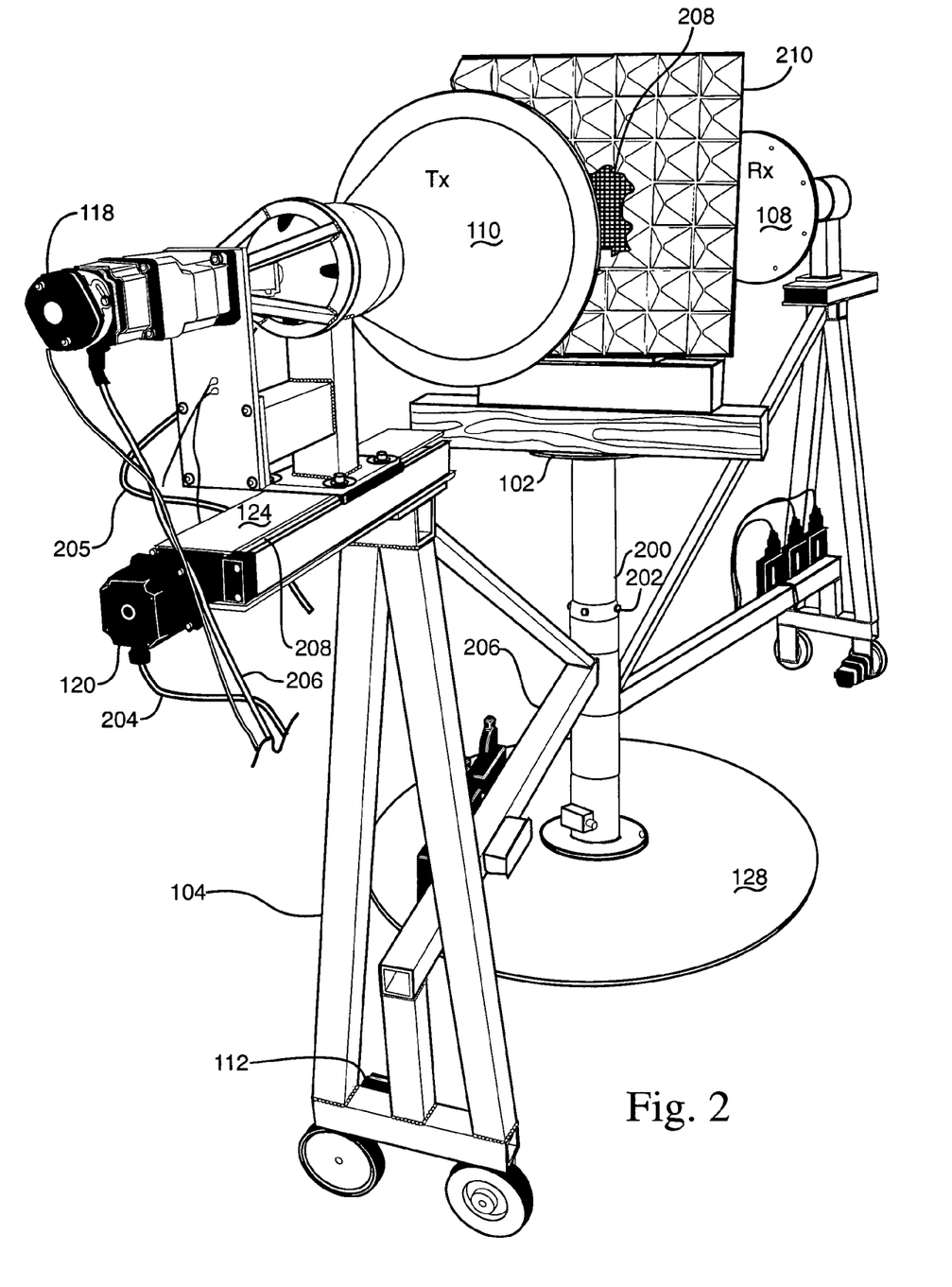
FIG. 2 shows additional details of the FIG. 1 apparatus.

FIG. 2 in the drawings especially shows additional details of one upright 104 and associated components of the FIG. 1 apparatus as these components appear from a different viewing angle, an angle closer to an axial bore alignment with the antenna horn 110. Especially visible in the FIG. 2 drawing is the sloping double column welded construction of the upright 104 and its manner of attachment to the azimuth movable radial arm 206. Also viewable in the FIG. 2 drawing are additional details of the drive motor assemblies 112, 118 and 120 for azimuth angle measurement, polarization angle measurement and energy focus adjustment functions respectively. The threaded screw accomplishing radial horn focus adjustments also appears partially at 208 in the FIG. 2 drawing.

Figure 4:
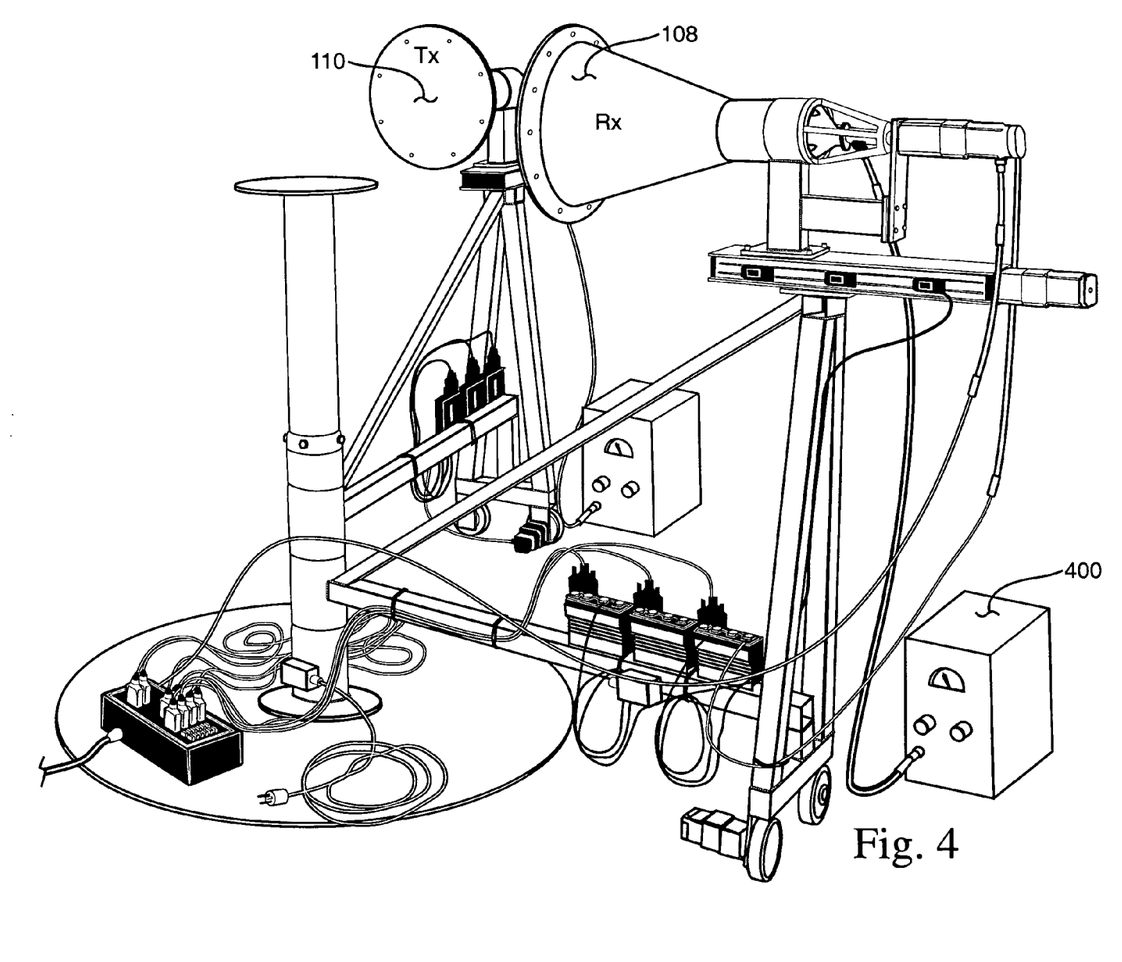
FIG. 4 shows an altered position additional view of the FIG. 1, FIG. 2 and FIG. 3 apparatus including a representative microwave output signal processor.

Also shown in the FIG. 2 drawing are more tangible but artificially terminated views of the multi conductor and coaxial cables as appear at 204 and 205 and serving to convey electrical energy and radio frequency signals between portions of the FIG. 1 apparatus and in the FIG. 2 apparatus. The function of these cables may be better appreciated from the additional discussions of signals in the apparatus appearing herein and from information provided by the manufacturers of e.g. drive components identified subsequently herein. FIG. 4 in the drawings also provides general indications of radio frequency signal cable functions in the invention. Otherwise, cable details are largely omitted herein in the interest of drawing clutter reduction and in view of the inherent functions performed.

The FIG. 2 drawing also shows at 208 a test target located on the sample supporting platform 102 and surrounded by an aperture containing baffle or shield member 210. The baffle or shield 210 may be comprised of high energy loss materials such as carbonaceous coated foam having pyramid surface features. Such material is often found in the absorbers disposed within anechoic chambers for example. The test target shown in FIG. 2 may be of the split ring and post resonant members type with each received in an array of cells. Such target is one of a large number of test articles that can be accommodated with the described apparatus. The structure represented at 208 is a material exhibiting a negative index of refraction once filled with split ring resonators at a frequency of about 9.3 GHz, about where the horns of the apparatus begin to cut off.

The microwave radio frequency antenna horns 108 and 110 are preferably provided with focusing lenses within the horn structure in order to realize from the energized horn 110 for example a small and well focused spot of near field output energy. Such energy may be directed to a selected sample location, a location near the center of an energized face of a test sample (a six inch spot at a 3 foot separation for example). In a similar manner the test sample modified energy receiver antenna horn 108 is also provided with a lens focused spot, a spot from which it collects a major part of the test sample modified microwave input energy sent to a receiver circuit. The focusing of these spots on input and output surfaces of a test material sample is assisted by the adjustments provided with the FIG. 1 linearly adjustable radio frequency horn positioning driven linear slides at 124 and 126. These adjustments also provide accommodation for changes in the desired focusing spot location resulting from possible consideration of both large and small sample sizes. Such lens inclusive microwave horn antennas are available in the commercial marketplace, one source of such devices is identified in the list of component parts and sources for the present invention included below herein.

Characterization system initialization is possible using intensity measuring laser diodes in order to affix a system starting point. Once the system is initialized and positional commands are sent to the device, feedback becomes a critical element as a result of internal motor skipping and drive wheels slipping on the floor. Feedback of locations along trajectory 134 is possible by way of a magnetic strip attached along the trajectory 134 and magnetic encoders attached to the movable arms 140 and 142 coincided with stepper motor encoders on drive motor assemblies 112 and 114. Via software, information from all encoders is manipulated in order to obtain the exact desired location within the user inputted tolerance levels. Feedback involving the polarization drive assemblies 118 and 116 is obtained by counting motor steps with the encoder via software. Feedback involving the horn to test sample separation at 126 and 124 is possible using homing and limit switches.

In the materials characterization apparatus of the FIG. 1 through FIG. 4 drawings the following specifically identified components may be conveniently used; other components may of course be substituted.

The characterization apparatus provides three axis sample measurement freedom. First axis freedom enables independent horn motion over a plane extending about 300 degrees around a center platform. This allows off axis sample measurements to be made. Second axis freedom achieves spot focusing of horn lens antennas; for this freedom the antenna horns are affixed to linear slides movable linearly back and forth in order to obtain maximum transmission and reception involving the tested material. Second degree freedom also accommodates differing sample sizes (greater than 12 inches cubed and weighing more than 150 pounds) The linear slides also aid in a software achieved semi-automatic-calibrating process (testing for point of maximum reflection). Third axis freedom enables horn rotation over 360 degrees around a central axis of each horn. Such polarization rotation of each horn independently allows further characterization of anisotropy in the medium under test.

Frame

The FIG. 1-FIG. 4 represented frame is disposed in pieces that may be disassembled and reassembled easily. Light weight welded aluminum of structural rigidity is preferred.

Software

The later herein disclosed computer software interfaces directly with an Agilent E8364B Network Analyzer (represented at 400 in FIG. 4) and with a Parker Compumotor 6k multi-axis controller system. All axes may be adjusted independently in the software. Initialization of each axis is managed though software functions as also aid in avoidance of element collisions. Data received via the network analyzer can be plotted in real time as a function of frequency, incidence angle, transmitted angle, and polarization angle.

Positioning

Encoders and sensors are used throughout the system to ensure measurement accuracy.

Component Information
1. Entrelec 2M PR30 DIN Rail-17322005
   Part Description: DIN Rail
   length: 3 feet
   Manufacturer: Entrelec
2. 6k6—Compumotor 6 Axis Controller
   Part Description: Control Box
   Quantity: 1
   Manufacturer: Parker Automation, Parker Hannifin Corp.
3. E8364B Network Analyzer
   Part Description: Network Analyzer
   Quantity: 1
   Manufacturer: Agilent Technologies
4. E-AC—Compumotor AC Stepper Drive
   Part Description: Step Drive
   Quantity: 6
   Manufacturer: Parker Automation, Parker Hannifin Corp.
5. 71-016137-10—Compumotor 6K to E-AC Cable
   Part Description: Cable
   Quantity: 8
   Manufacturer: Parker Automation, Parker Hannifin Corp.
6. 404T09XEMS-VLD2H3L2C3M3E1B1R11P1—Parker Daedal 404 Series Table
   Part Description: Linear Slide
   Quantity: 2
   Manufacturer: Parker Automation, Parker Hannifin Corp.
7. HV232-01-10—Compumotor HV Series Motor
   Part Description: Stepper Motor
   Quantity: 2
   Manufacturer: Parker Automation, Parker Hannifin Corp.
8. HV232-01-10-PX23-030—Compumotor HV Series Motor With Mounted Bayside Gearhead
   Part Description: Stepper Motor With 30:1 Gearhead
   Quantity: 2
   Manufacturer: Parker Automation, Parker Hannifin Corp.
9. 260-NT10L1000RHV2 J00SF2CE—Encoder Products Incremental Thru Bore Encoder
   Description: Stepper Motor Encoder
   Quantity: 2
   Manufacturer: Encoder Products Company
10. VM25—Compumotor I/O Module with Cable
    Description: Limit Switch Module
    Quantity: 1
    Manufacturer: Parker Automation, Parker Hannifin Corp.
11. HV232-01-10-PX23-010—Compumotor HV Series Motor With Mounted Bayside Gearhead, 10:1 ratio
    Description: Stepper Motor With 10:1 Gearhead
    Quantity: 2
    Manufacturer: Parker Automation, Parker Hannifin Corp.
12. E3X-DA11-s—Digital Fiber Optic Amplifier, NPN Output, pre-wired 2m cable
    Description: Fiber Optic Sensor Amplifier
    Quantity: 4
    Manufacturer: OMRON
13. E32-TC200E—General Purpose Fiber Optic With M3 Mounting Heads
    Description: Fiber Optic Cable
    Quantity: 4
    Manufacturer: OMRON
14. 90-014-240—True Blue 0.290", (2)-SMA-SP
    Description: Coax Cable
       Operating Frequency: 18 GHz Max
       Insertion Loss 10 GHz: 4.1817 dB
       Insertion Loss 18 GHz: 5.7741 dB
    Quantity: 2
    Length: 20 ft
    Manufacturer: STORM
15. QLA-SMAC12Z01—12" Spot Focusing Lens Antenna
    Description: Spot Focusing Horn Lens Antenna
       Spot Diameter: <6" at 3'
       Frequency Range: 8.2-18 GHz
       At 8.2 GHz: 26.5 dB gain
       At 18 GHz: 33.4 dB gain
       Connector: SMA female
    Quantity: 2
    Manufacturer: Quinstar Technology, Inc.

16. VDR-75-24-24VDC 7W Power Supply. 110VAC Input
    Description: DC Power Supply
    Quantity: 1
    Manufacturer: Mean Well
17. LME5F-3—5 Micron Resolution Linear Encoder Readhead. 3M Cable
    Description: Magnetic Strip Encoder
    Quantity: 2
    Manufacturer: Parker Automation, Parker Hannifin Corp.
18. LMS5-XXX—Linear Encoder Magnetic Scale XXX Indicates Measuring Length+40 mm
    Description: Magnetic Strip Encoder
    Length: 4 feet
    Manufacturer: Parker Automation, Parker Hannifin Corp.

Measurements of signal polarization changes caused by transmission or reflection of a microwave signal during test are important with respect to electronic materials. Polarization changes are of particular importance in materials having negative coefficient characteristics because these properties are relatively unknown with negative index medias and are still being discovered and applied in cutting edge technology. The ability of present invention apparatus to accommodate a large range of polarization changes from signal encounter with a sample and to accommodate such 360 degree polarization changes during unattended automated sample testing is a significant aspect of the invention. Signal polarization changes incurred during operation of the FIG. 1, FIG. 2 and FIG. 3 apparatus may be detected with use of an instrument such as the vector responsive Agilent Network Analyzer identified as component 3 in the above listing herein. This instrument is coupled to the receiver horn antenna 108 or 110 in the FIG. 4 drawing.

Figure 3:
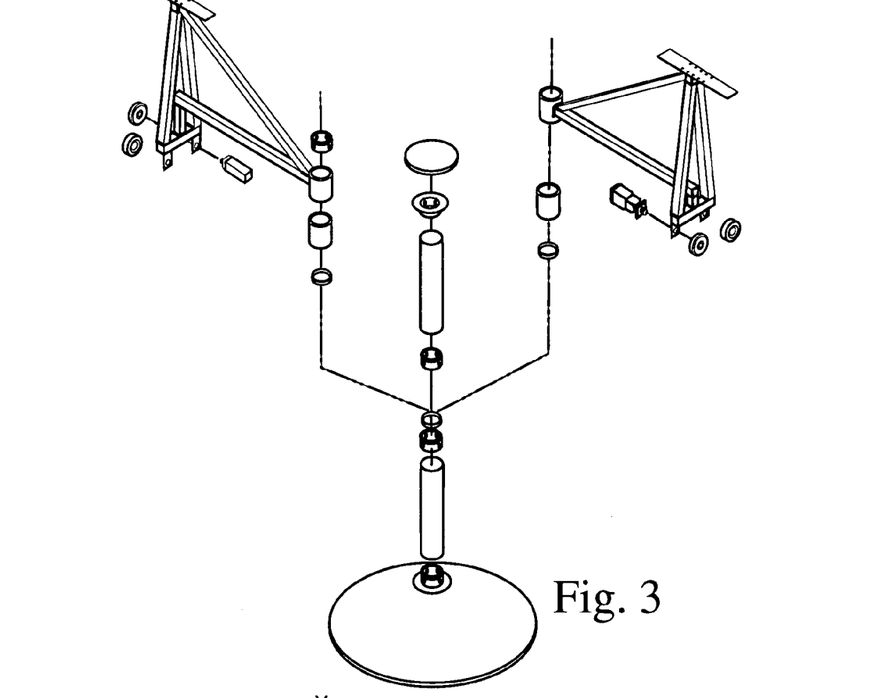
FIG. 3 shows details of FIG. 1 and FIG. 2 structural elements relating to the invention.

Collection storage and processing of microwave radio frequency signals from a transducer, such as the horn 108 in the FIG. 1 through FIG. 3 drawings, is also accomplished in the systems disclosed in a number of issued patents; moreover these collected signals have also been used in the determination of electrical material characteristics in certain issued U.S. patent documents. Such signal collection and use is for examples disclosed in the U.S. Pat. Nos. 6,674,292, 6,788, 244; 6,842,010; 6,859,046 and 7,057,743. These U.S. patents are included in the list of references submitted with this document and are also hereby incorporated by reference herein.

The ability to determine characteristics of electrical material samples in an automated manner following operator initiation of the process; the ability to determine negative index material characteristics such as negative index responses to magnetic fields and electric fields (e.g. material permeability characteristics and material permittivity or dielectric constant characteristics for example); the use of near field microwave horn sample energization and the use of focused microwave material energization are each believed to be particularly notable accomplishments of the present invention in comparison with previous material characterizations.

In accordance with Section 1.52 of title 37 in the United States Code of Federal Regulations and sections 608.05 etc. in the Eighth Edition, fifth revision dated August 2006 of the U.S. Patent and Trademark Office Manual of Patent Examining Procedures, each current at the time of filing the present document as an Application for Letters Patent of the United States, applicants herewith submit Compact Disc-Recordable (CD-R) listings of a software suite usable to control and appropriately energize the multiple drive motors of the heretofore disclosed present invention apparatus.

This software suite is submitted in the form of two identical discs identified as "Copy 1" and "Copy 2". The contents of these discs are hereby incorporated by reference herein.

The computer code in these listings may be converted into the steps of human comprehensible source code for the "C#" computer language with use of the commonly available Microsoft "Notepad" decoding software using a Microsoft prepared personal computer system. Additional details regarding this software are disclosed in the transmittal letter accompanying these discs. This letter is also hereby incorporated by reference herein.

In the following paragraphs there is disclosed what is in essence an operator instruction manual document providing insight regarding use and capabilities of a software controlled automated near field focusing horn beamed, spot microwave energy responsive electrical material examination apparatus as described herein. This apparatus is given the name "Megatron SCRIPTRONIC" or "Megatron" for purposes of this paraphrased instruction document and the disc disclosed software.

1 Introduction. Controlling a Megatron is accomplished with the included software suite. This document outlines use of this software to create useful measurements.

2 Megatron SCRIPTRONIC 2.1 Introduction

Megatron SCRIPTRONIC allows the user to create arbitrarily complex measurement scenarios.

The Megatron software provides a series of windows for control of the device. The first of these windows includes three main areas:

the 3D Megatron model view,
the properties view of the selected event, and
the event list view.

The majority of script creation happens in the event list view. This is where one will place events that define the motion of the Megatron parts. The properties view is where setting of parameters such as how far a certain event will move the Megatron and which S-parameters the appended network analyzer will measure.

The Megatron model view simply reflects what the motion defined will do to the Megatron.

2.2 Script Creation Example

Making a measurement script.

2.3 Defining Measurement Parameters

First, we need to define what is to be measured. Each measurable parameter is defined in Table 1 below.

TABLE 1

| Parameter | Value |
| --- | --- |
| S11 | Yes |
| S12 | No |
| S21 | No |
| S22 | Yes |
| Delay | No |
| Imaginary | No |
| Linear Magnitue | No |
| Log Magnitude | Yes |
| Phase | No |
| Real | No |
| SWR | No |
| Points | 401 |
| Start Frequency | 8 GHz |
| Stop Frequency | 18 GHz |

Once these parameters are decided, they can be entered into SCRIPTRONIC. First, we need to start the program. Next, we add a Start Event either by clicking the top most rectangle in the event list view or by Events—Add—Start on the menu bar. Now, if we click on the Start Event in the event list view, the properties area of the window shows all of the measurement parameters enterable

2.4 Defining Motion

In this example measurement we simply want to sweep one of the arms around the center, taking measurements every 0.5 degree. Before this, there is need to move the horn antennae into position, 36" away from the center column. We will use two Move Events and then some Step and repeat events to accomplish this. First, we will add two Move Events to move the horns 36" from the center. The horns home to a position 37.5" from the center; thus both of these events need to simply move their horn 1.5" towards the center. Move Events may be created in the same way the Start Event was created. One may either click on the Red rectangle in the event list view or click Events—Add—Move. Once there are two Move Events in the event list view, there is need to set their parameters. For this, set one of the Move Event's Axis to LinearSlide 1 and the other to LinearSlide 2. Then, set the Destination field for each Event to 1.5, which corresponds to 1.5" towards the center.

Now, we need to create a loop in the script that moves Arm 2 by 270 degrees. First, add a Step Event to the event list. Set the event Axis to Arm 2, and it's Step Size to 0.5. Now, add a Repeat Event, set it's Axis to Arm 2, right click on the Repeat event, click Connect, click on the Step event, and then set the Step event's EndValue to 270. This makes the script continue performing the action defined in the Connection of the repeat node until the condition in the EndValue is met. In this example, this means that the Megatron will continue stepping Arm 2 by 0.5 degrees until the arm position is greater than or equal to 180.

2.5 Simulation

An interesting aspect of the Megatron SCRIPTRONIC is that one can observe exactly what the real-life Megatron is going to accomplish when the script just created is applied. One can simulate what this script will accomplish by pressing the "Simulate" button in the 3D view. This example will take significant time to execute since it requires many steps to move 270 degrees in half degree steps.

2.6 Conclusion

Now that this script file has been created, we can use it over and over again to achieve the same measurement in different scenarios. Save the script file; it will be used it in the next section.

3 Megatron ACTUATOR

3.1 Introduction

Megatron ACTUATOR is the second program in the Megatron software suite. ACTUATOR can bee used to make the Megatron apparatus and the connected network analyzer perform physical measurements. In this section, this is demonstrated.

Megatron ACTUATOR

3.2 Startup

Megatron requires special care during startup to ensure that all components are in the correct positions. The following steps are required to correctly start and position Megatron.

Run Megatron ACTUATOR
Connect to Megatron and Network Analyzer
Click the connect button
Perform automatic homing
Click the home button
Release the axes
Click the pause button Now, to fine tune the homing routine, physically move the arms against the stops.

With arms in the correct position, press the manual homing button
Click the button WITH NO ICON Now everything is in position and script file from the previous section may be applied to Megatron System Control

3.3 Automatic Script Execution

Opening of script file, setting the path for ACTUATOR to put data and allowing Megatron to run are all that is needed to execute the script created in Section 2.

Any object may be located on the center platform 102, with nothing on the platform, a baseline characterization of the room will result. Upon completion Megatron will have performed an accurate measurement that would have required hours or even days if accomplished by hand.

4 Conclusion

The afore recited tutorial therefore has proceeded from no measurements to a full blown electromagnetic characterization of a selected object.

We have therefore disclose herein an automated, spot focusing near field microwave evaluation of negative index of refraction electromagnetic materials that may involve negative permeability and negative permittivity characteristics. Utility of the disclosed apparatus and method with additional materials is practical.

The foregoing description of the preferred embodiment has been presented for purposes of illustration and description. It is not intended to be exhaustive or to limit the invention to the precise form disclosed. Obvious, modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular scope of the invention as determined by the appended claims when interpreted in accordance with the breadth to which they are fairly, legally and equitably entitled.

We claim:

1. Near field, focusing horn beamed, spot microwave energy responsive material examination apparatus comprising the combination of:

a plurality of focused microwave transducer horn antenna elements each disposed on a distinct, selected trajectory, first drive type responsive, movable support element of said material examination apparatus;

a focused spot material sample capturing apparatus to capture a microwave energy responsive material sample, the capturing apparatus being disposed in a central near field location with respect to the selected trajectory of said horn antenna elements;

each of said selected trajectory first drive type responsive movable support elements further including a second drive type apparatus to drive said respective transducer horn antenna element a radial distance with respect to said material sample capturing apparatus and a third drive type apparatus to drive said respective microwave transducer horn antenna element signal about a polarization angle;

a first of said microwave transducer horn antenna elements being a source of microwave energy spot focused on said microwave energy responsive material sample and a second of said microwave transducer horn antenna elements comprising a microwave receiver apparatus also spot focused on said microwave energy responsive material sample with one of said focused microwave transducer horn antenna elements being first drive type responsive around said trajectory with respect to another of said focused microwave transducer horn antenna elements; and programmed electronic computer apparatus connected with said first second and third drive types and in established sequence control of said material examination apparatus following an operator initiation event;

said first drive type responsive movable elements and related of said antenna horn elements being position adjustable in response to both positive index and negative index electromagnetic characteristic determined signals received from said energy responsive material sample.

2. The near field focusing horn beamed, spot microwave energy responsive material examination apparatus of claim 1 wherein said focused microwave transducer horn antenna elements include a first spot focused microwave energy transmitter horn antenna element and a second spot focused microwave energy receiving horn antenna element each disposed on a circumferentially accessed element of said material examination apparatus.

3. The near field focusing horn beamed, spot microwave energy responsive material examination apparatus of claim 1 wherein positive index and negative index electromagnetic characteristic determined signals relate to one of magnetic field responsive characteristics and electrical field responsive characteristics of said material sample.

4. The near field focusing horn beamed, spot microwave energy responsive material examination apparatus of claim 3 wherein said magnetic field responsive characteristics and electrical field responsive characteristics include permeability, permittivity and anisotropy characteristics of said material sample.

5. The near field focusing horn beamed, spot microwave energy responsive material examination apparatus of claim 1 wherein said microwave transducer horn antenna elements each include a microwave lens element adjacent a signal communication port thereof.

6. The near field focusing horn beamed, spot microwave energy responsive material examination apparatus of claim 1 wherein said first drive type, said second drive type and said third drive type each include a stepping motor electrical to mechanical transducer.

7. The near field focusing horn beamed, spot microwave energy responsive material examination apparatus of claim 1 wherein said second of said microwave transducer horn antenna elements comprises a microwave receiver apparatus is responsive to one of microwave electromagnetic energy reflected from said captured material sample and microwave energy refracted during transmission through said captured material sample.

8. The near field focusing horn beamed, spot microwave energy responsive material examination apparatus of claim 1 wherein said horn antenna elements selected trajectory is coincident and circular in shape for each of said horn antenna elements.

9. A near field, computer controlled free space spot microwave materials examination method comprising the steps of:

mounting a sample of the materials adjacent a focal point of a near field sample illuminator and a near field sample emissions receptor adapted to travel along a closed travel trajectory azimuth path;

illuminating said mounted sample with waveguide generate near field spot focused microwave energy of selected wavelength, selected radiation pattern, selected polarization angle and selected azimuth angle with respect to said mounted sample;

driving one of said near field sample illuminator and said near field sample emissions receptor through plural positions along said closed travel trajectory azimuth path under operator initiated computer control while collecting sample determined emissions;

recording a data sequence of said sample determined emissions found along said closed travel trajectory azimuth path and trajectory path position identifications relating thereto in response to achievement of a plurality of driven positions along said travel trajectory path;

said achieved plurality of driven positions along said travel trajectory path including positions determined by negative index of refraction related electromagnetic characteristics in said near field free space examined materials; and examining said data sequence of sample determined emissions and trajectory path positions relating thereto for emission amplitude and trajectory path angular position relating data characteristic of said near field free space examined materials.

10. The near field, computer controlled free space spot microwave materials examination method of claim 9 wherein said collecting of sample determined emissions includes collecting one of sample reflecting emissions and sample refracting emissions from said mounted sample.

11. The near field, computer controlled free space spot microwave materials examination method of claim 9 wherein said step of illuminating said mounted sample with waveguide generated near field spot focused microwave energy includes the step of supplying said illuminating microwave energy from a lens focusing horn waveguide operating below cutoff microwave frequency.

12. The near field, computer controlled free space spot microwave materials examination method of claim 9 wherein said step of examining said data sequence of sample determined emissions and trajectory path positions relating thereto is responsive to one of sample permittivity, sample permeability, sample refraction index and sample anisotropy determined microwave signals.

13. The near field, computer controlled free space spot microwave materials examination method of claim 9 further including driving said sample illuminator through a plurality of sample electromagnetic characteristics related positions along said closed travel trajectory azimuth path.

14. The near field, computer controlled free space spot microwave materials examination method of claim 9 further including driving said sample receptor through a plurality of sample electromagnetic characteristics related positions along said closed travel trajectory azimuth path.

15. The near field, computer controlled free space spot microwave materials examination method of claim 9 wherein at least one of said sample emissions receptor and said sample illuminator is driven through a plurality of computer controlled polarization sensing horn axial rotational positions at a plurality of discrete positions along said closed travel trajectory azimuth path.

16. Near field, free space, focused microwave energy spot, negative refractive index inclusive material examination apparatus comprising the combination of:

sample mounting apparatus holding a captive sample of said material in selected orientation adjacent focal points of a sample illuminator apparatus and a sample signal receptor apparatus disposed about closed travel trajectory paths;

said sample illuminator apparatus energizing said captive sample from along a first of said travel trajectory paths with spot focused microwave radiant energy of selected wavelength and selected polarization angle;

said sample signal receptor apparatus responsive to reflected and emitted electromagnetic signals received from said sample along a second of said trajectory paths;

selectively energizable electrical driving apparatus moving one of said sample illuminator apparatus and said sample signal receptor apparatus through plural positions along said respective travel trajectory paths while sample determined emissions are collected;

said plural positions along said first and second travel trajectory paths including one of sample reflected and sample refracted output signal trajectory positions determined by one of negative permeability and negative permittivity characteristics in said captive sample;

storing apparatus receiving a sequence of sample determined emissions and trajectory path positions data in response to achieving one of a plurality of differing sample illumination and signal reception positions from along one of said travel trajectory paths;

correlation apparatus examining said storing apparatus data for received signal amplitude and trajectory path angular position relating data characteristic of said near field free space examined materials.

17. The near field, free space, focused microwave energy spot, negative refractive index inclusive material examination apparatus of claim 16 wherein each of said sample illuminator apparatus and said sample signal receptor apparatus is driven along a closed travel trajectory path during operation of said apparatus.

18. The near field, free space, focused microwave energy spot, negative index refractive inclusive material examination apparatus of claim 16 wherein one of said sample illuminator apparatus and said sample signal receptor apparatus is held in fixed position along a closed travel trajectory path during operation of said apparatus.

19. The near field, free space, focused microwave energy spot, negative refractive index inclusive material examination apparatus of claim 16 wherein said sample illuminator apparatus and said sample signal receptor apparatus closed travel trajectory paths are coincident.

20. The near field, free space, focused microwave energy spot, negative refractive index inclusive material examination apparatus of claim 16 further including additional of said electrical driving apparatus moving one of said sample illuminator apparatus and said sample signal receptor apparatus through additional axes defined positions along said respective travel trajectory paths while sample determined emissions are collected.

21. The near field, free space, focused microwave energy spot, negative refractive index inclusive material examination apparatus of claim 16 wherein said selectively energizable electrical driving apparatus further includes rotational driving apparatus connected with one of said sample illuminator apparatus and said sample signal receptor apparatus and controlling horn axis polarization pattern determining rotational position thereof.

22. The near field, free space, focused microwave energy spot, negative refractive index inclusive material examination apparatus of claim 21 wherein said selectively energizable electrical driving apparatus connected with one of said sample illuminator apparatus and said sample signal receptor apparatus is connected with each of said sample illuminator apparatus and said sample signal receptor apparatus disposing each said apparatus in independent, computer controlled, rotational position within a 360 degree azimuthal rotational range.

23. The near field, free space, focused microwave energy spot, negative refractive index inclusive material examination apparatus of claim 16 wherein said storing apparatus is responsive to one of permeability, permittivity and anisotropy characteristic signals received along one of said travel trajectory paths.

24. The near field, free space, focused microwave energy spot, negative index refractive inclusive material examination apparatus of claim 16 wherein said plural positions along said respective travel trajectory paths include both sample reflected and sample refracted output signal trajectory positions determined by one of negative permeability and negative permittivity characteristics in said captive sample.

25. A near field spot microwave energy method of characterizing an anisotropic electromagnetic material comprising the steps of:

illuminating a mounted sample of said anisotropic electromagnetic material from a controllably movable horn antenna source of spot microwave energy;

moving to a plurality of sequentially accessed collection horn antenna azimuth positions disposed in anisotropic signal physical locations and polarization orientations around said mounted sample with a computer driven, collection horn antenna moving apparatus supporting a collection horn antenna;

collecting a plurality of sample determined microwave energy signals during movement to said plurality of sequentially accessed collection of horn antenna azimuth positions;

including in said computer driven, collection horn antenna moving apparatus a plurality of antenna positions and polarization orientations selected to obtain sample determined microwave energy signals to provide at least one of a negative index of refraction, negative permittivity and negative permeability sample determined microwave energy signals; and determining characteristics of said mounted sample in response to azimuth location, azimuth extent, polarization orientation and amplitude of said negative index of refraction, negative permittivity and negative permeability included sample determined microwave energy signals.

26. The near field spot microwave energy method of characterizing an anisotropic electromagnetic material of claim 25 wherein said plurality of collection horn antenna azimuth positions is performed in closed loop response to polarization orientation, sample negative index of refraction, negative permittivity and negative permeability sample determined microwave energy signals received in said collection horn antenna.

27. The near field spot microwave energy method of characterizing an anisotropic electromagnetic material of claim 25 wherein said plurality of collection horn antenna azimuth positions disposed in anisotropic signal physical locations and polarization orientations around said mounted sample are identified in response to one of polarization orientation, sample negative index of refraction, negative permittivity and negative permeability determined sample microwave energy signals received in said collection horn antenna.

* * * * *